United States Patent [19]
Huffman

[11] Patent Number: 5,470,359
[45] Date of Patent: Nov. 28, 1995

[54] REGULATORY ELEMENT CONFERRING TAPETUM SPECIFICITY

[75] Inventor: Gary A. Huffman, Des Moines, Iowa

[73] Assignee: Pioneer Hi-Bred Internation, Inc., Des Moines, Iowa

[21] Appl. No.: 230,929

[22] Filed: Apr. 21, 1994

[51] Int. Cl.⁶ .............................. A01H 1/00; C12N 15/00; C12N 15/05
[52] U.S. Cl. .......................... 47/58; 435/172.3; 536/23.1; 536/24.1
[58] Field of Search .................................... 800/200, 205; 47/58.03, 58.05; 435/240.4, 145.49, 172.3; 536/26, 23.1, 24.1; 935/61, 23.1

[56] References Cited

U.S. PATENT DOCUMENTS

| | | | |
|---|---|---|---|
| 5,086,169 | 2/1992 | Mascarenhas | 536/27 |
| 5,196,525 | 3/1993 | McPherson et al. | 536/24.1 |

FOREIGN PATENT DOCUMENTS

| | | |
|---|---|---|
| 0578611A1 | 1/1994 | European Pat. Off. |
| 92/05261 | 4/1992 | WIPO |
| 92/11379 | 7/1992 | WIPO |
| 92/13957 | 8/1992 | WIPO |
| 93/02197 | 2/1993 | WIPO |

OTHER PUBLICATIONS

Arias, Jonathan A. et al., "Dissection of the Functional Architecture of a Plant Defense Gene Promoter Using a Homologous in Vitro Transcription Initiation System", *The Plant Cell*, vol. 5: pp. 485–496 (Apr. 1993).
Benfey, Philip N. et al., "Tissue-specific expression from CaMV 35S enhancer subdomains in early stages of plant development", *The EMBO Journal*, vol. 9, No. 6: pp. 1677–1684 (1990).
Benfey, Philip N. et al., "Combinatorial and synergistic properties of CaMV 35S enhancer subdomains", The EMBO Journal, vol. 9, No. 6: pp. 1685–1696 (1990).
Bruce, Wesley B., et al. "*cis*–Acting Elements Involved in Photoregulation of an Oat Phytochrome Promoter in Rice", The Plant Cell, vol. 2: pp. 1081–1089 (Nov. 1990).
Dzelzkalns, Valdis A. et al., "Distinct *cis*–Acting Elements Direct Pistil–Specific and Pollen–Specific Activity of the Brassica S Locus Glycoprotein Gene Promoter", The Plant Cell, vol. 5.: pp. 855–863 (Aug. 1993).
Guerrero, Felix D. et al., "Promoter sequences from a maize pollen–specific gene direct tissue–specific transcription in tobacco", Mol. Gen. Genet., vol. 224: pp. 161–168 (1990).
Hamilton, Douglas A. et al., "Dissection of a pollen–specific promoter from maize by transient transformation assays", Plant Molecular Biology, vol. 18: pp. 211–218 (1992).
Hartley, Robert W., "Barnase and Barstar: Expression of Its Cloned Inhibitor Permits Expression of a Cloned Ribonuclease", J. Mol. Biol., vol. 202: pp. 913–915 (1988).
Huffman, Gary A. et al., "Analysis of a Tapetum–specific Promoter from Maize", J. Cell. Biochem. Suppl. 17B: Abstract D209 (1993).
Mariani, Celestina et al., "Induction of male sterility in plants by a chimaeric ribonuclease gene", Nature, vol. 347: pp. 737–741 (Oct. 25, 1990).
Mariani, Celestina et al., "A chimaeric ribonuclease–inhibitor gene restores fertility to male sterile plants", Nature, vol. 357: pp. 384–387 (Jun. 4, 1992).
McCormick, Sheila et al., "Anther–specific genes: Molecular Characterization and Promoter Analysis in Transgenic Plants", Plant Reproduction: From Floral Introduction to Pollination, Lord et al. (eds.), The American Society of Plant (List continued on next page.)

*Primary Examiner*—Gary Benzion
*Attorney, Agent, or Firm*—Foley & Lardner

[57] ABSTRACT

A novel DNA regulatory element that confers anther tapetum-specific gene expression has been discovered, isolated, and characterized. The tapetum-specific regulatory element can be used to control the expression of a foreign gene that disrupts the function of tapetal cells. Thus, the control of maize pollen production can be achieved by using the tapetum-specific regulatory element to produce male-sterile plants. Various methods can be used to restore male fertility in the F1 generation of such male-sterile plants.

20 Claims, 9 Drawing Sheets

OTHER PUBLICATIONS

Physiologists Symposium Series, vol. 1: pp. 128–135 (1989).

Spena, A. et al., "Anter–specific expression of the *rolB* gene of *Agrobacterium rhizogenes* increases IAA content in anthers and alters anther development and whole flower growth", Theor. Appl. Genet., vol. 84: pp. 520–527 (1992).

Twell, David et al., "Pollen–specific gene expression in transgenic plants: coordinate regulation of two different tomato gene promoters during microsporogensis", Development vol. 109, pp. 705–713 (1990).

Twell, David et al., "Promoter analysis of genes that are coordinately expressed during pollen development reveals pollen–specific enhancer sequences and shared regulatory elements", Genes & Development vol. 5: pp. 496–507, (1991).

van der Meer, Ingrid M. et al., "Promoter analysis of the chalcone synthase (chsA) gene of *Petunia hybrida*: a 67 bp promoter region directs flower–specific expression", Plant Molecular Biology, vol. 15: pp. 95–109 (1990).

van der Meer, Ingrid M. et al., "Antisense Inhibition of Flavonoid Biosynthesis in Petunia Anthers Results in Male Sterility", The Plant Cell, vol. 4: pp. 253–262, (Mar, 1992).

Xu, Huiling, "Haploid and diploid expression of a *Brassica campestris* anther–specific gene promoter in *Arabidopsis* and tobacco", Mol. Gen. Genet., vol. 239: pp. 58–65 (1993).

De Block et al. *Planta* vol. 189 pp. 218–225 (Mar. 1993).

Van T'Veer et al. PNAS vol. 89. pp. 8971–8975 (1992).

FASTDB Search of Seq ID #1 & #2.

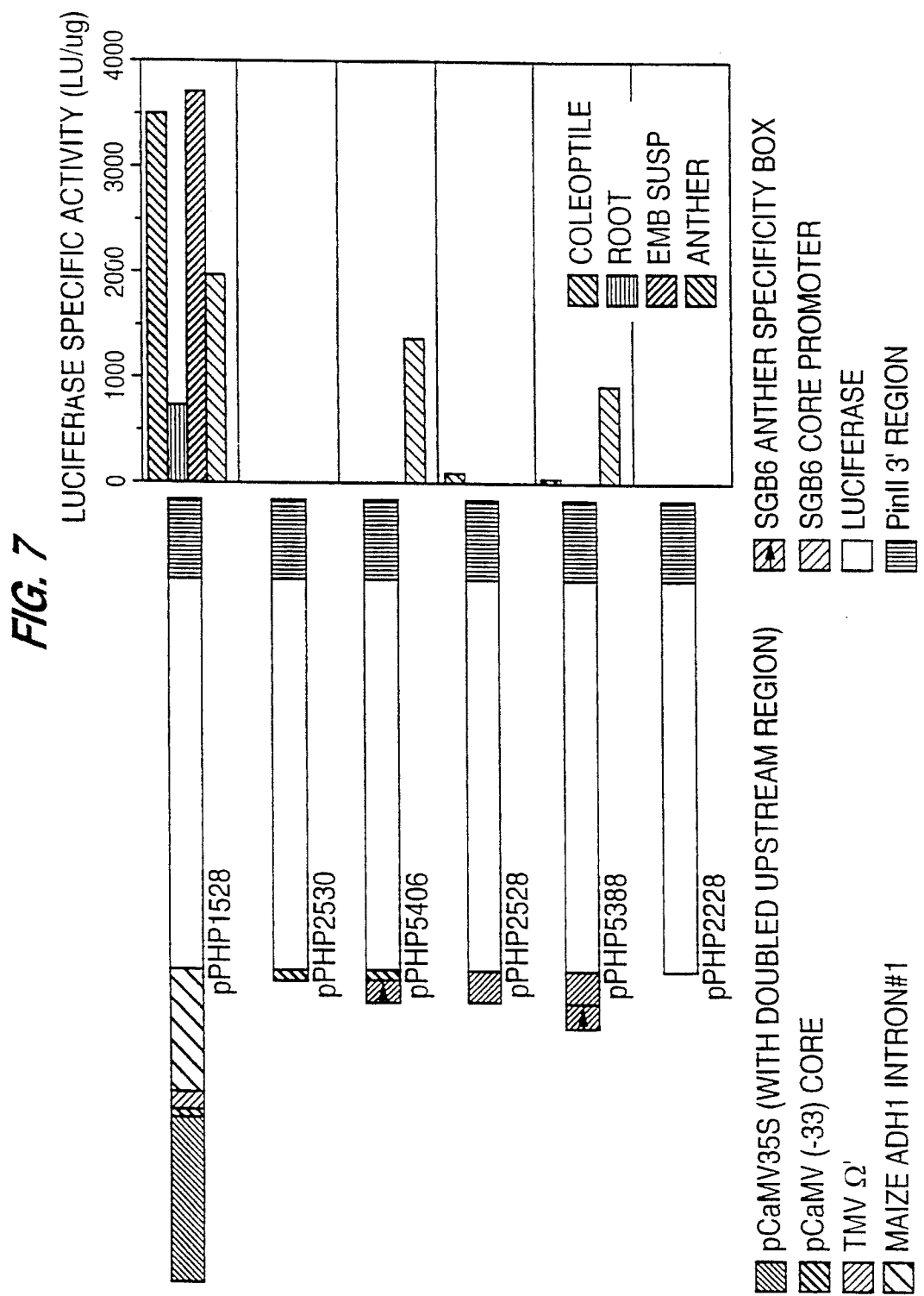

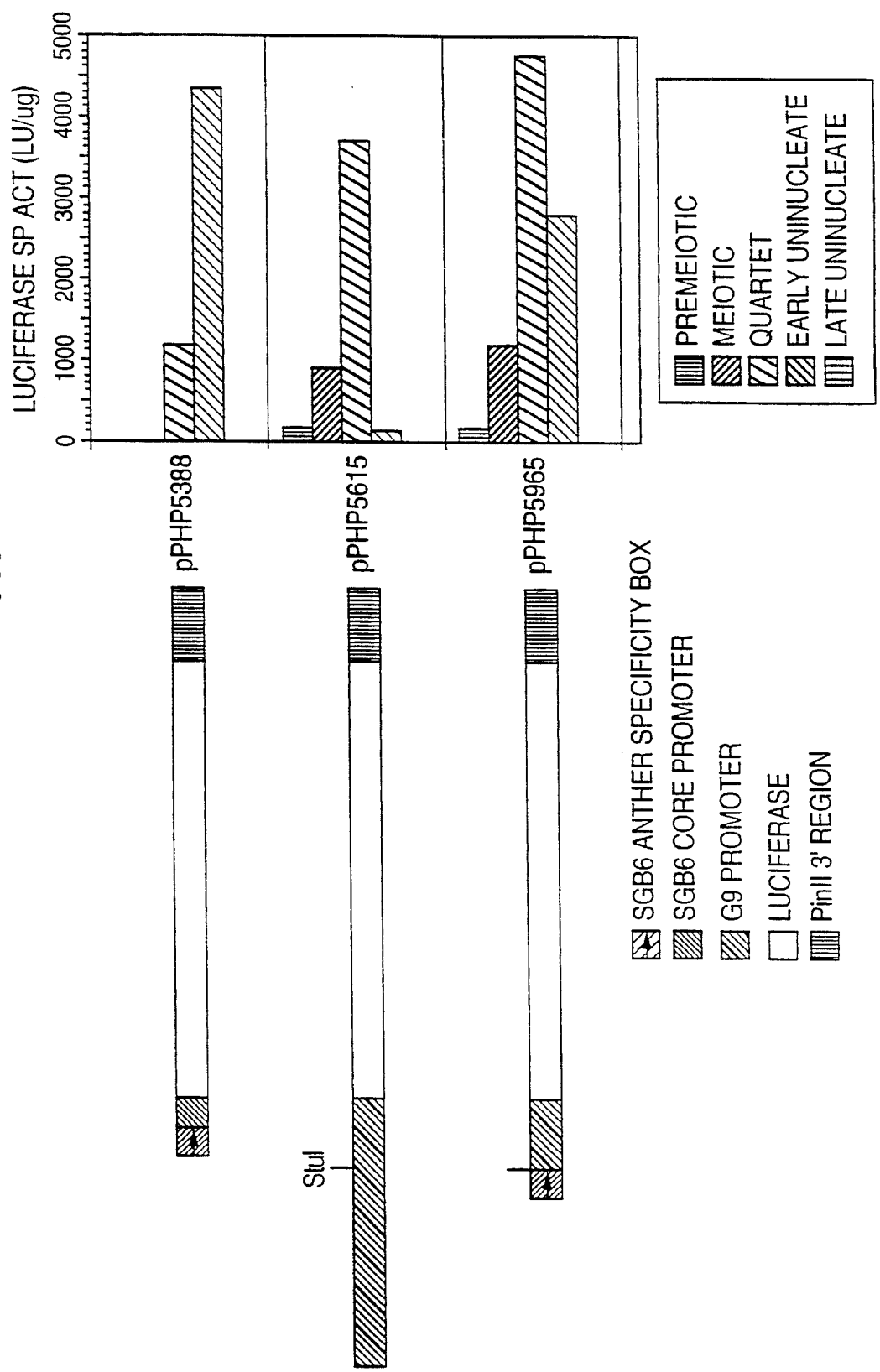

FIG. 9

NUCLEOTIDE SEQUENCE OF THE G9 PROMOTER

```
  1  CCTTCGAACG  AACGGTACTG  TAAAAATACG  GTAGCTCAGA  TTTGTGATTT
 51  CAATTCGATT  CGGGTCTCCT  GGCTGGATGA  AACCGATGCG  AGAGAAGAAA
101  AAAAAATTGT  TGCATGTAGT  TGGCGCCTGT  CACCCAACCA  AACCAGTAGT
151  TGAGGCACGC  CCTGTTTGCT  CACGATCACG  AACGTACAGC  ACTATAAAAC
201  ACGCAGGGAC  TGGAAAGCGA  GATTTCACAG  CTGAAACGAG  CCAAAACGCA
251  GAAGCTGCAC  TGCATACATC  GAGCTAACTA  TCTGCAGCCA  TG
```

REGULATORY ELEMENT CONFERRING TAPETUM SPECIFICITY

BACKGROUND OF THE INVENTION

1. Field of the Invention

The present invention relates to novel regulatory elements which confer tapetum-specificity to gene expression. In particular, this invention is directed to a tapetum-specific regulatory element of the maize SGB6 gene, and to using such a regulatory element to produce transgenic, male-sterile plants. Moreover, this invention is directed to a method for restoring male fertility in the progeny of male-sterile plants.

2. Background

Control of pollen fertility is essential in hybrid crop production. In hybrid maize production, control of pollen fertility is typically accomplished by physically removing the male inflorescence, or tassel, prior to pollen shed. Manual detasseling is highly labor intensive. Although mechanical detasseling is less labor intensive than manual detasseling, mechanical detasseling is less reliable and requires subsequent examination of the crop and possibly, remedial manual detasseling. Both methods of detasseling cause a loss of yield.

Pollen fertility also can be controlled by applying a chemical composition to the plant or soil to prevent pollen production in female plants. See, for example, Ackmann et al., U.S. Pat. No. 4,801,326. According to this method, hybrid seeds are produced by the cross fertilization of the treated female plants with pollen from non-treated plants. However, the chemical approach is labor intensive, and presents potential problems with the toxicity of chemicals introduced into the environment.

Another approach to the control of fertility is based upon the use of a cytoplasmic gene(s) for male sterility. See, for example, Patterson, U.S. Pat. No. 3,861,079. The problem with this approach, however, is that the expression of certain cytoplasmic male sterility genes is accompanied by increased susceptibility to fungal pathogens. For example, extensive use of one cytotype, cmsT, led to an epiphytic outbreak of Southern Corn Leaf Blight in the early 1970's. Although additional cms cytotypes have become available, their use has not become widespread due to the concern over possible susceptibility to the Southern Corn Leaf Blight pathogen, or to other, as yet unknownpathogens.

A need therefore exists for a method to control pollen production without reliance on naturally occurring male sterility genes or, the traditional manual, mechanical, and chemical methods.

SUMMARY OF THE INVENTION

Accordingly, it is an object of the present invention to provide a method to produce male-sterile maize plants using an expression vector that disrupts the function of anther tapetal cells.

It is a further object of this invention to provide a DNA regulatory element that confers tapetum-specific gene expression.

These and other objects are achieved, in accordance with one embodiment of the present invention by the provision of an isolated DNA molecule, wherein the DNA molecule comprises a nucleotide sequence selected from the group consisting of (a) SEQ ID NO: 1, (b) a nucleotide sequence that has substantial sequence similarity with SEQ ID NO: 1; and (c) fragments of (a) or (b), wherein the DNA molecule is a tapetum-specific regulatory element.

In accordance with another embodiment of the present invention, there has been provided an expression vector comprising a tapetum-specific regulatory element. Such an expression vector may include a promoter which is under the control of the tapetum-specific regulatory element. An example of one type of promoter is a DNA molecule which is selected from the group consisting of (a) SEQ ID NO: 2; (b) a nucleotide sequence that has substantial sequence similarity with SEQ ID NO: 2; and (c) fragments of (a) or (b), wherein the DNA molecule is a promoter of an anther-specific gene, which is expressed during the meiotic to quartet stages of development.

In accordance with a further embodiment of the present invention, there has been provided an expression vector comprising a foreign gene, wherein the expression of the foreign gene is under the control of a tapetum-specific regulatory element, and wherein the product of the foreign gene disrupts the function of tapetal cells.

In accordance with a further embodiment of the present invention, there has been provided a method of using such an expression vector to produce a male-sterile plant, comprising the step of introducing an expression vector into embryogenie plant cells, wherein the foreign gene of the expression vector is selected from the group consisting of a structural gene, an antisense gene, a ribozyme gene and an external guide sequence gene.

In accordance with a further embodiment of the present invention, there has been provided a method of using a tapetum-specific regulatory element to produce a male-fertile hybrid plant, comprising the steps of:

(a) producing a first parent male-sterile plant comprising an expression vector that comprises a tapetum-specific regulatory element, a promoter, and a first foreign gene, wherein the tapetum-specific regulatory element conjunction with the promoter control the expression of the first foreign gene, and wherein the product of the first foreign gene disrupts the function of tapetal cells;

(b) producing a second parent plant comprising an expression vector that comprises a tapetum-specific regulatory element, a promoter and a second foreign gene, wherein the tapetum-specific regulatory element in conjunction with the promoter control the expression of the second foreign gene; and (c) cross-fertilizing the first parent with the second parent to produce a hybrid plant, wherein the tapetal cells of the hybrid plant express the second foreign gene, and wherein the product of the second foreign gene prevents the disruption of tapetal function by the product of the first foreign gene, thereby producing a male-fertile hybrid plant.

BRIEF DESCRIPTION OF THE DRAWINGS

FIG. 7 presents studies on the induction of luciferase activity in anthers, coleoptiles, roots and in a maize embryonic suspension by a control plasmid or by test plasmids.

FIG. 8 presents studies on the induction of luciferase activity in anthers by the 94 base pair tapetum-specific regulatory element (SGB6 Anther Specificity Box), by a promoter of an anther-specific gene, which is expressed during the meiotic to quartet stages of development (G9 Promoter), or by a combination of the SGB6 Anther Specificity Box and G9 Promoter.

FIG. 9 presents the nucleotide sequence of the 289 base pair G9 promoter [SEQ ID NO: 2].

DETAILED DESCRIPTION OF PREFERRED EMBODIMENTS

1. Definitions

Figure 1:
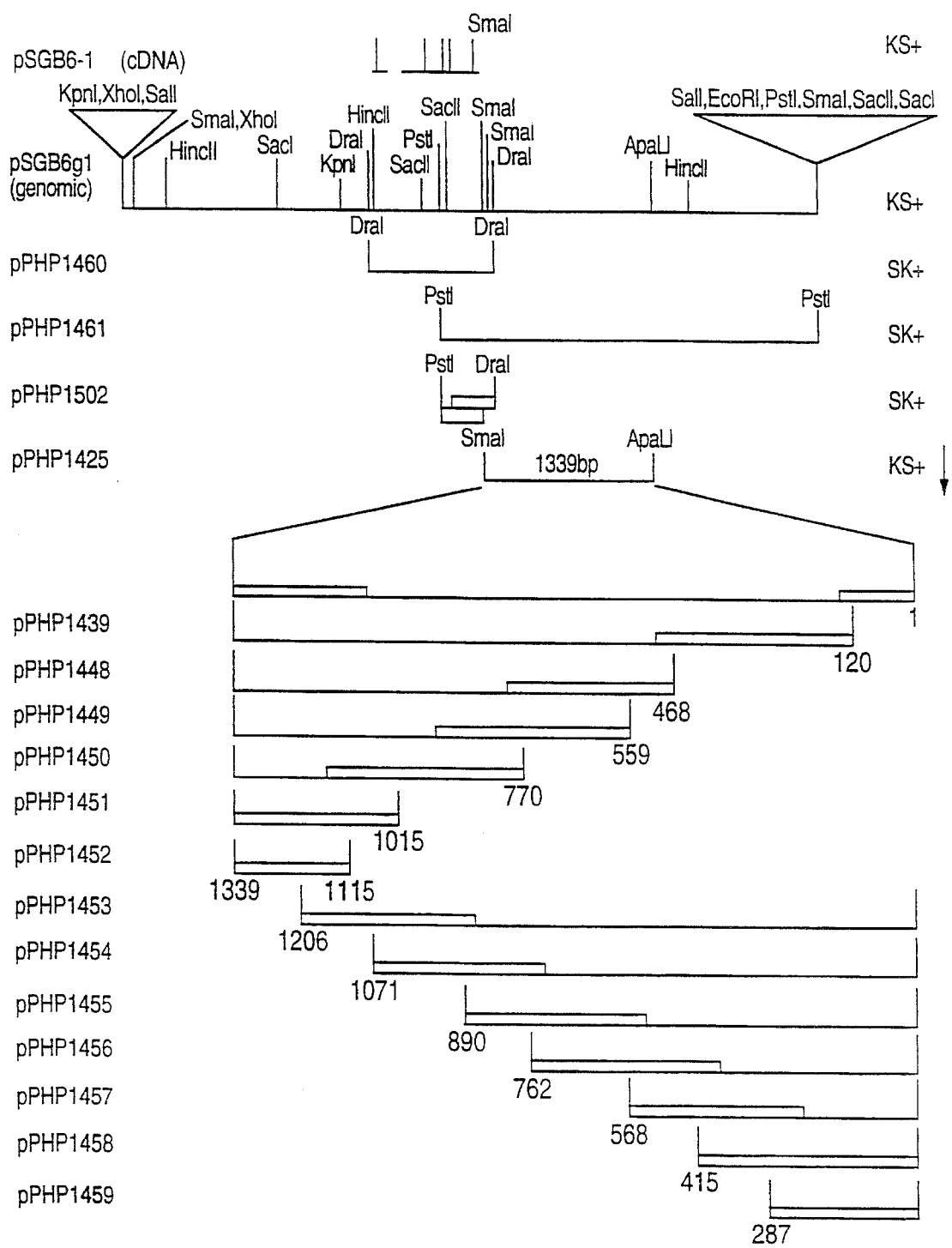
FIG. 1 presents strategies used to sublcone and sequence the upstream region of the SGB6 maize anther tapetum clone. SGB6 DNA fragments were subcloned in either pBluescript® KS+ or pBluescript® SK+ (Stratagene Cloning Systems; La Jolla, Calif.).

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypspride.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

A core promoter contains essential nucleotide sequences for promoter function, including the TATA box and start of transcription. By this definition, a core promoter may or may not have detectable activity in the absence of specific sequences that may enhance the activity or confer tissue specific activity. For example, the SGB6 core promoter consists of about 37 nucleotides 5'-ward of the transcriptional start site of the SGB6 gene, while the Cauliflower Mosaic Virus (CaMV) 35S core promoter consists of about 33 nucleotides 5'-ward of the transcriptional start site of the 35S genome.

A tapetum-specific regulatory element is a DNA sequence that directs a higher level of transcription of an associated gene in anther tapetal tissue than in some or all other tissues of a plant. For example, the SGB6 gene, described herein, is expressed in tapetal cells. The tapetum-specific regulatory element of the SGB6 gene can direct the expression of a foreign gene in anther tissue, but not in root tissue or coleoptile tissue. Thus, the 94 base pair tapetum-specific regulatory element of the SGB6 gene is referred to as the "SGB6 Anther Specifity Box."

An operator is a DNA molecule that is located 5'-ward of a structural gene and that contains a nucleotide sequence which is recognized and bound by a repressor protein. The binding of a repressor protein with its cognate operator results in the inhibition of the transcription of the structural gene. For example, the LexA gene encodes a repressor protein that binds to the LexA operator.

An isolated DNA molecule is a fragment of DNA that is not integrated in the genomic DNA of an organism. For example, the tapetum-specific regulatory element is a DNA fragment that has been separated from the genomic DNA of an inbred maize plant. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A foreign gene refers in the present description to a DNA sequence that is operably linked to at least one heterologous regulatory element. For example, any gene other than the SGB6 structural gene is considered to be a foreign gene if the expression of that gene is controlled by a tapetum-specific regulatory element of the SGB6 gene.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A ribozyme is an RNA molecule that contains a catalytic center. The term includes RNA enzymes, self-splicing RNAs, and self-cleaving RNAs. A DNA sequence that encodes a ribozyme is termed a ribozyme gene.

An external guide sequence is an RNA molecule that directs the endogenous ribozyme, RNase P, to a particular species of intracellular mRNA, resulting in the cleavage of the mRNA by RNase P. A DNA sequence that encodes an external guide sequence is termed an external guide sequence gene.

Two nucleic acid molecules are considered to have a substantial sequence similarity if their nucleotide sequences share a similarity of at least 50%. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO(R) BLAST Network Service. See Altschul et al., *J. Mol. Biol.* 215:403 (1990). Also, see Pasternak et al., "Sequence Similarity Searches, Multiple Sequence Alignments, and Molecular Tree Building," in METHODS IN PLANT MOLECULAR BIOLOGY AND BIOTECHNOLOGY, Glick et al. (eds.), pages 251–267 (CRC Press, 1993).

2 Isolation of a Regulatory Element from a Tapetum-Specific Gene

The use of genetic engineering to effect an alteration in the phenotypic expression of a plant in a tissue-specific manner is well-known in the art. One approach to control pollen production is to manipulate gene expression in the tapetum. The tapetum is a layer of cells that surrounds microsporogenous cells in the anther and provides nutrients, such as reducing sugars, amino acids and lipids to the developing microspores. Reznickova, *C.R. Acad. Bulg. Sci.* 31:1067 (1978); Nave et al., *J. Plant Physiol.* 125:451 (1986); Sawhney et al., *J. Plant Physiol.* 125:467 (1986). Tapetal cells also produce β(1,3)-glucanase ("callase") which promotes microspore release. Mepham et al., *Protoplasma* 70:1 (1970). Therefore, a delicate relationship exists between the tapetum and the microsporogenous cells, and any disruption of tapetal function is likely to result in dysfunctional pollen grains. In fact, lesions in tapetal biogenesis are known to result in male sterility mutants. Kaul, "Male Sterility in Higher Plants," in MONOGRAPHS ON THEORETICAL AND APPLIED GENETICS, Vol. 10, Frankel et al. (eds.), pages 15–95 (Springer Verlag, 1988). Thus, a failure of the microspores to develop into mature pollen grains can be induced using a recombinant DNA molecule that comprises a gene capable of disrupting tapetal function under the control of tapetum-specific regulatory sequences.

Anther-specific promoters and genes are known in the art. See, for example, McCormick et al., "Anther-Specific Genes: Molecular Characterization and Promoter Analysis in Transgenic Plants," in PLANT REPRODUCTION: FROM FLORAL INDUCTION TO POLLINATION, Lord et al. (eds.), pages 128–135 (1989); Scott et al., International Application Publication No. WO 92/11379 (1992); van der Meer et al., *The Plant Cell* 4:253 (1992). However, there are no generally accepted principles or structural criteria for recognizing DNA sequences that confer anther specificity, especially tapetum specificity, to gene expression in maize. Consequently, it is not possible to isolate a tapetum-specific regulatory element directly from a maize genomic library by screening for a consensus sequence that confers tapetum-specific gene expression.

The novel tapetum-specific regulatory element of the present invention was discovered upstream of DNA sequences that encode the maize SGB6 gene, as described below. The regulatory element was obtained by isolating cDNA molecules that encode tapetum-specific genes and then, using the cDNAs as probes to identify corresponding genes in a suitable genomic library.

A. Isolation of cDNA Molecules Encoding Tapetum-Specific Genes

The first step in the construction of a cDNA library containing tapetum-specific genes is to isolate total RNA from anther tissue. Preferably, the source of anther tissue is two to six inch long tassels which contain tapetal tissue in various stages of development including stages in which the tapetum plays a critical role in microspore release. Most preferably, the source of anther tissue is two to six inch long tassels of the maize inbred B73 line.

Total RNA can be prepared from the tassels using techniques well-known to those in the art. In general, RNA isolation techniques must provide a method for breaking plant cells, a means of inhibiting RNase-directed degradation of RNA, and a method of separating RNA from DNA, protein, and polysaccharide contaminants. For example, total RNA can be isolated from tassels by freezing plant tissue in liquid nitrogen, grinding the frozen tissue with a mortar and pestle to lyse cells, extracting the ground tissue with a solution of phenol/chloroform to remove proteins, and separating RNA from the remaining impurities by selective precipitation with lithium chloride. See, for example, Ausubel et al. (eds.), CURRENT PROTOCOLS IN MOLECULAR BIOLOGY, pages 4.3.1–4.3.4 (1990). Also, see Sharrock et al., *Genes and Development* 3:1745 (1989).

Alternatively, total RNA can be isolated from tassels by extracting ground tissue with guanidinium isothiocyanate, extracting with organic solvents, and separating RNA from contaminants using differential centrifugation. See, for example, Strommer et al., "Isolation and characterization of Plant mRNA," in METHODS IN PLANT MOLECULAR BIOLOGY AND BIOTECHNOLOGY, Glick et al. (eds.), pages 49–65 (CRC Press, 1993).

In order to construct a cDNA library, poly(A)+ RNA must be isolated from a total RNA preparation. Poly(A)+ RNA can be isolated from total RNA by using the standard technique of olgo(dT)-cellulose chromatography. See, for example, Strommer et al., supra.

Double-stranded cDNA molecules are synthesized from poly(A)+ RNA using techniques well-known to those in the art. See, for example, Ausubel et al., supra, at pages 5.5.2–5.6.8. Moreover, commercially available kits can be used to synthesize double-stranded cDNA molecules. For example, such kits are available from GIBCO/BRL (Gaithersburg, Md.), Clontech Laboratories, Inc. (Palo Alto, Calif.), Promega Corporation (Madison, Wis.) and Stratagene Cloning Systems (La Jolla, Calif.).

Various cloning vectors are appropriate for the construction of a tassel cDNA library. For example, a cDNA library can be prepared in a vector derived from bacteriophage, such as a λgt10 vector. Huynh et al., "Constructing and Screening cDNA Libraries in λgt10 and λgt11," in *DNA Cloning: A Practical Approach, Vol. I*, Glover (ed.), pages 49–78 (IRL Press, 1985).

Alternatively, double-stranded cDNA molecules can be inserted into a plasmid vector, such as a pBluescript® vector (Stratagene Cloning Systems; La Jolla, Calif.), or other commercially available vectors. Suitable cloning vectors also can be obtained from the American Type Culture Collection (Rockville, Md.).

In order to amplify the cloned cDNA molecules, the cDNA library is inserted into a procaryotic host, using standard techniques. For example, the tassel cDNA library can be introduced into competent *E. coli* DH5 cells, which can be obtained from GIBCO/BRL (Gaithersburg, Md.).

Differential screening can be used to isolate cDNA clones encoding anther-specific genes from the cDNA library. For example, single-stranded cDNA probes can be synthesized in the presence of radioactive nucleotides using poly(A)+ RNA isolated from either tassels or seedlings. cDNA clones that hybridize with tassel cDNA probe, but not with the seedling cDNA probe, are isolated for further analysis. The technique of differential screening is well-known to those in the art. See, for example, Sargent, "Isolation of Differentially Expressed Genes," in GUIDE TO MOLECULAR CLONING TECHNIQUES, Berger et al. (eds.), pages 423–432 (Academic Press, 1987); Tedder et al., *Proc. Natl. Acad. Sci. USA* 85:208 (1988).

The basic approach for obtaining tapetum-specific cDNA clones can be modified by constructing a subtracted cDNA library which is enriched in anther-specific cDNA clones. Hedrick et. al., Nature 308:149 (1984). For example, double-stranded cDNA with EcoRI ends can be prepared from tassel RNA and mixed with a 50-fold excess of small, blunt-ended cDNA fragments prepared from seedling RNA. The mixture of cDNAs is heated to melt double-stranded cDNA, single-stranded cDNAs are allowed to hybridize, and double-stranded cDNA molecules are inserted into the EcoRI site of a cloning vector. Under these conditions, the only tassel cDNA molecules that are likely to regenerate double-stranded fragments with an EcoRI site at each end are those cDNAs that lack complementary fragments in the seedling cDNA. Ausubel et al., supra, at pages 5.8.9.–5.8.15.

cDNA clones can be analyzed using a variety of techniques such as restriction analysis, Northern analysis, and in situ hybridization.

B. Isolation of Tapetum-Specific Genes from a Genomic Library

The methodology, described above, can be used to isolate cDNA clones encoding proteins that are expressed in anther tissue, but not in seedling tissue. The cDNA clones are used as probes to isolate the corresponding genes from a genomic library.

A plant genomic DNA library can be prepared by means well-known in the art. See, for example, Slightom et al. "Construction of λ Clone Banks," in METHODS IN PLANT MOLECULAR BIOLOGY AND BIOTECHNOLOGY, Glick et al. (eds.), pages 121–146 (CRC Press, 1993). A preferred source of plant genomic DNA is maize DNA. Genomic DNA can be isolated from maize tissue, for example, by lysing plant tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient. Ausubel et al., supra, at pages 2.3.1–2.3.3.

DNA fragments that are suitable for the production of a genomic library can be obtained by the random shearing of genomic DNA or by the partial digestion of genomic DNA with restriction endonucleases. See, for example, Ausubel et al., supra, at pages 5.3.2–5.4.4, and Slightom et al., supra.

Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are disclosed by Slightom et al., supra, and are well-known in the art. Also see Ausubel et al., supra, at pages 3.0.5–3.17.5.

Alternatively, a maize genomic library can be obtained commercially. Preferably, such a library is an EMBL3 genomic library derived from a Sau3A partial digest of genomic DNA isolated from the inbred maize line W22 (Clontech Laboratories, Inc.; Palo Alto, Calif.).

A library containing genomic clones is screened with one or more anther-specific cDNA clones using standard techniques. See, for example, Ausubel et al., supra, at pages 6.0.3–6.6.1; Slightom et al., supra; Raleigh et al., *Genetics* 122:279 (1989).

C. Identification of a Tapetum-Specific Regulatory Element

Genomic clones can be analyzed using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel et al., supra, at pages 4.8.1–4.8.5; Walmsley et al , . "Quantitative and Qualitative Analysis of Exogenous Gene Expression by the S1 Nuclease Protection Assay," in METHODS IN MOLECULAR BIOLOGY, VOL. 7: GENE TRANSFER AND EXPRESSION PROTOCOLS, Murray (ed.), pages 271–281 (Humana Press Inc. 1991). However, structural analysis per se cannot lead to the identification of a tapetum-specific regulatory element associated with the cloned gene because a model for maize tapetum-specific regulatory sequences has not been developed. Thus, the regulatory element must be identified using functional analysis.

The general approach of such functional analysis involves subcloning fragments of the genomic clone into an expression vector which contains a reporter gene, introducing the expression vector into various maize tissues, and assaying the tissue to detect the transient expression of the reporter gene. The presence of a tapetum-specific regulatory element in the genomic subclone is verified by the observation of reporter gene expression in anther tissue, and the absence of reporter gene expression in non-anther tissue.

Methods for generating fragments of a genomic clone are well-known. Preferably, enzymatic digestion is used to form nested deletions of genomic DNA fragments. See, for example, Ausubel et al., supra, at pages 7.2.1–72.20; An et al., "Techniques for Isolating and Characterizing Transcription Promoters, Enhancers, and Terminators," in METHODS IN PLANT MOLECULAR BIOLOGY AND BIOTECHNOLOGY, Glick et al. (eds.), pages 155–166 (CRC Press, 1993).

As an example, the possibility that the regulatory element resides "upstream," or 5'-ward, of the transcriptional start site can be tested by subcloning a DNA fragment that contains the upstream region, digesting the DNA fragment in either the 5' to 3' direction or in the 3' to 5' direction to produce nested deletions, and subcloning the small fragments into expression vectors for transient expression. This general approach is illustrated in Example 1, below.

The selection of an appropriate expression vector will depend upon the method of introducing the expression vector into host cells. Typically, an expression vector contains: (1) prokaryotic DNA elements coding for a bacterial replication origin and an antibiotic resistance marker to provide for the growth and selection of the expression vector in the bacterial host; (2) eukaryotic DNA elements that control initiation of transcription, such as a promoter; (3) DNA elements that control the processing of transcripts, such as a transcription termination/polyadenylation sequence; and (4) a reporter gene that is operably linked to the DNA elements that control transcription initiation. Useful reporter genes include β-glucuronidase, β-galactosidase, chloramphenicol acetyl transferase, luciferase, and the like. Preferably, the reporter gene is either the β-glucuronidase (GUS) gene or the luciferase gene. General descriptions of plant expression vectors and reporter genes can be found in Gruber et al., "Vectors for Plant Transformation," in METHODS IN PLANT MOLECULAR BIOLOGY AND BIOTECHNOLOGY, Glick et al. (eds.), pages 89–119 (CRC Press, 1993). Moreover, GUS expression vectors and GUS gene cassettes are available from Clontech Laboratories, Inc. (Palo Alto, Calif.), while luciferase expression vectors and luciferase gene cassettes are available from Promega Corporation (Madison, Wis.).

Expression vectors containing test genomic fragments can be introduced into protoplasts, or into intact tissues or isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993), and by Phillips et al., "Cell/Tissue Culture and In Vitro Manipulation," in CORN AND CORN IMPROVEMENT, 3rd Edition, Sprague et al. (eds.), pages 345–387 (American Society of Agronomy, Inc. et al. 1988). Methods of culturing plant tissues are illustrated in Examples 1 and 2.

Methods of introducing expression vectors into plant tissue include the direct infection or co-cultivation of plant tissue with *Agrobacterium tumefaciens*. Horsch et al., *Science* 227:1229 (1985). Descriptions of Agrobacterium vector systems and methods for Agrobacterium-mediated gene transfer are provided by Gruber et al., supra, and Miki et al., supra.

Preferably, expression vectors are introduced into maize tissues using a direct gene transfer method such as microprojectile-mediated delivery, DNA injection, electroporation, and the like. See, for example, Gruber et al., supra; Miki et al., supra; Klein et al., *Biotechnology* 10:268 (1992). More preferably, expression vectors are introduced into maize tissues using microprojectile-mediated delivery with a biolistic device. This method of delivery is illustrated in Examples 1–3, below.

The above-described methods have been used to identify DNA sequences that regulate gene expression in a tapetum-specific manner. In particular, a tapetum-specific regulatory element was found to reside within a 94 base pair DNA fragment which is defined by nucleotides 583 to 490 upstream of the SGB6 start site of transcription. The nucleotide sequence of the 94 base pair tapetum-specific regulatory element is:

(−583) ACAGTTCACT AGATATGCAT GATCTTTAAC AAT-
TGCTGCT TGTCAAGTGA TCTATACGTA CTAGAAATTG
TTAACGACGA

GGATTGTGCG GTTTCTTTTG GCACAAATGG CATGAA-
CAGA CCTAACACGC CAAAGAAAAC CGTGTTTACC
GTACTTGTCT

GTAATCCGGG ACGC (−490) [SEQ ID NO: 1]. CATTAGGCCC
TGCG

Thus, the present invention encompasses a DNA molecule having a nucleotide sequence of SEQ ID NO: 1 and having the function of a tapetum-specific regulatory element.

Variants of the 94 base pair tapetum-specific regulatory element can be produced by deleting, adding and/or substituting nucleotides for the nucleotides recited in SEQ ID NO: 1. Such variants can be obtained, for example, by oligonucleotide-directed mutagenesis, linker-scanning mutagenesis, mutagenesis using the polymerase chain reaction, and the like. Ausubel et al., supra, at pages 8.0.3–8.5.9. Also see generally, McPherson (ed.), DIRECTED MUTAGENESIS: A PRACTICAL APPROACH, IRL Press (1991). Thus, the present invention also encompasses DNA molecules comprising nucleotide sequences that have substantial sequence similarity with SEQ ID NO: 1 and function as a tapetum-specific promoter.

Moreover, additional deletion analyses can be performed to further localize one or more tapetum-specific regulatory elements within the 94 base pair tapetum-specific regulatory element. Thus, the present invention also encompasses fragments of the DNA molecule having nucleotide sequence of SEQ ID NO: 1, as long as the DNA fragments function as a tapetum-specific regulatory element.

3. Use of a Tapetum-Specific Regulatory Element to Control Pollen Production

A. Production of Male-Sterile Plants

An object of the present invention is to provide a means to control pollen production using a tapetum-specific regulatory element. Importantly, the SGB6 tapetum-specific regulatory element can induce the expression of a heterologous gene in tapetal cells of anthers from the quartet stage to the mid-uninucleate stage of development. The practical significance of such timing is that the expression of a sterility-inducing gene during this developmental stage will disrupt anther maturation early enough to permit visual verification of the function of the sterility-inducing system in the field. Thus, the effects of the sterility-inducing gene would be evident in the production field at a sufficiently early stage of development to allow either manual or mechanical detasseling of any "fertile escapees" that result from a partial or total breakdown of the sterility-inducing system.

One general approach to induce male sterility is to construct an expression vector in which the tapetum-specific regulatory element is operably linked to a nucleotide sequence that encodes a protein capable of disrupting tapetal cell function. Proteins capable of disrupting tapetal function include proteins that inhibit the synthesis of macromolecules that are essential for cellular function, enzymes that degrade macromolecules that are essential for cellular function, proteins that alter the biosynthesis or metabolism of plant hormones, and proteins that inhibit a specific function of tapetal cells.

For example, an expression vector can be constructed in which the tapetum-specific regulatory element is operably linked to a nucleotide sequence that encodes an inhibitor of protein synthesis. Diphtheria toxin, for example, is a well-known inhibitor of protein synthesis in eukaryotes. DNA molecules encoding the diphtheria toxin gene can be obtained from the American Type Culture Collection (Rockville, Md.), ATCC No. 39359 or ATCC No. 67011.

Alternatively, the disruption of tapetal function can be achieved using DNA sequences that encode enzymes capable of degrading a biologically important macromolecule. For example, Mariani et al., *Nature* 347:737 (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Quaas et al., *Eur. J. Biochem.* 173:617 (1988), describe the chemical synthesis of the RNase-T1, while the nucleotide sequence of the barnase gene is disclosed in Hartley, *J. Molec. Biol.* 202:913 (1988).

RNase-T1 and barnase genes may be obtained, for example, by synthesizing the genes with mutually priming long oligonucleotides. See, for example, Ausubel et al., supra, at pages 8.2.8 to 8.2.13. Also, see Wosnick et al., *Gene* 60:115 (1987). Moreover, current techniques using the polymerase chain reaction provide the ability to synthesize genes as large as 1.8 kilobases in length. Adang et al., *Plant Molec. Biol.* 21:1131 (1993); Bambot et al., *PCR Methods and Applications* 2:266 (1993).

In an alternative approach, pollen production is inhibited by altering the metabolism of plant hormones, such as auxins. For example, the rolB gene of *Agrobacterium rhizogenes* codes for an enzyme that interferes with auxin metabolism by catalyzing the release of free indoles from indoxyl-β-glucosides. Estruch et al., *EMBO J.* 11:3125 (1991). Spena et al., *Theor. Appl. Genet.* 84:520 (1992), have shown that the anther-specific expression of the rolB gene in tobacco resulted in plants having shrivelled anthers in which pollen production was severely decreased. Therefore, the rolB gene is an example of a gene that is useful for the control of pollen production. Slightom et al., *J. Biol. Chem.* 261:108 (1985), disclose the nucleotide sequence of the rolB gene.

The control of pollen production also can be achieved by inhibiting a specific function of tapetal cells. For example, tapetal cells produce β(1,3)-glucanase, or callase, which promotes microspore release. Mepham et al., *Protoplasma* 70:1 (1970). A premature or late appearance of callase during the development of the tapetum is associated with certain types of male sterility. Warmke et al., *J. Hered.* 63:103 (1972). Therefore, the callase gene can be used to disrupt tapetal cell function. Scott et al., PCT International Application Publication No. WO 93/02197 (1993), disclose the nucleotide sequence of a tapetum-specific callase.

In order to express a protein that disrupts tapetal function, an expression vector is constructed in which a DNA sequence encoding the protein is operably linked to DNA sequences that regulate gene transcription in a tapetal-specific manner. The general requirements of an expression vector are described above in the context of a transient expression system. Here, however, the objective is to introduce the expression vector into plant embryonic tissue in such a manner that a foreign protein will be expressed at a later stage of development in the tapetum of the adult plant. Mitotic stability can be achieved using plant viral vectors that provide epichromosomal replication.

An alternative and preferred method of obtaining mitotic stability is provided by the integration of expression vector sequences into the host chromosome. Such mitotic stability can be provided by the microprojectile delivery of an expression vector to embryonic tissue as illustrated in Example 3, below.

Transcription of the foreign gene may be controlled by a promoter of a tapetum-specific gene or by a viral promoter, such as a Cauliflower Mosaic Virus (CaMV) promoter, a Figwort Mosaic Virus promoter, and the like. Gruber et al., supra. Preferably, the promoter is a promoter of a tapetum-specific gene or the CaMV 35S core promoter. More preferably, the promoter is a promoter of a tapetum-specific gene and in particular, the SGB6 core promoter, as described below.

Alternatively, transcription of the foreign gene may be controlled by a promoter of an anther-specific gene, which is expressed during the meiotic to quartet stages of development. In this way, foreign gene expression during meiosis through the mid-uninucleate stage can be achieved by using a tapetum-specific regulatory element in conjunction with such a promoter, as illustrated in Example 4. Preferably, the 289 base pair G9 promoter is used to extend the developmental window of heterologous expression, as described below.

In order to select transformed cells, the expression vector contains a selectable marker gene, such as a herbicide resistance gene. For example, such genes may confer resistance to phosphinothricine, glyphosate, sulfonylureas, atrazine, or imidazolinone. Preferably, the selectable marker gene is the phosphinothricine resistance gene. Although the expression vector can contain cDNA sequences encoding a foreign protein under the control of a tapetum-specific regulatory element, as well as the selectable marker gene under control of constitutive promoter, the selectable marker gene is preferably delivered to host cells in a separate selection expression vector. Such a "co-transformation" of embryonic tissue with a test expression vector containing a tapetum-specific regulatory element and a selection expression vector is illustrated in Example 3, below.

In an alternative approach, male sterility can be induced by the use of an expression vector in which the tapetum-specific regulatory element is operably linked to a nucleotide sequence that encodes an antisenseRNA. The binding of antisense RNA molecules to target mRNA molecules results in hybridization arrest of translation. Paterson, et al., *Proc. Natl. Acad. Sci. USA*, 74:4370 (1987). Thus, a suitable antisense RNA molecule would have a sequence that is complementary to that of a mRNA species encoding a protein that is necessary for tapetal cell function.

For example, the production of callase antisense RNA would inhibit the production of the callase enzyme which is essential for microspore release. In addition, male sterility can be induced by the inhibition of flavonoid biosynthesis using an expression vector that produces antisense RNA for the 3' untranslated region of chalcone synthase A gene. van der Meer et al., *The Plant Cell* 4:253 (1992). The cloning and characterization of the chalcone synthase A gene is disclosed by Koes et al., *Gene* 81:245 (1989), and by Koes et al., *Plant Molec. Biol.* 12:213 (1989).

Alternatively, an expression vector can be constructed in which the tapetum-specific regulatory element is operably linked to a nucleotide sequence that encodes a ribozyme. Ribozymes can be designed to express endonuclease activity that is directed to a certain target sequence in a mRNA molecule. For example, Steinecke et al., *EMBO J.* 11:1525 (1992), achieved up to 100% inhibition of neomycin phosphotransferase gene expression by ribozymes in tobacco protoplasts. More recently, Perriman et al., *Antisense Research and Development* 3:253 (1993), inhibited chloramphenicol acetyl transferase activity in tobacco protoplasts using a vector that expressed a modified hammerhead ribozyme. In the context of the present invention, appropriate target RNA molecules for ribozymes include mRNA species that encode proteins essential for tapetal function, such as callase mRNA.

In a further alternative approach, expression vectors can be constructed in which a tapetum-specific regulatory element directs the production of RNA transcripts capable of promoting RNase P-mediated cleavage of target mRNA molecules. According to this approach, an external guide sequence can be constructed for directing the endogenous ribozyme, RNase P, to a particular species of intracellular mRNA, which is subsequently cleaved by the cellular ribozyme. Altman et al., U.S. Pat. No. 5,168,053. Yuan et al., *Science* 263: 1269 (1994). Preferably, the external guide sequence comprises a ten to fifteen nucleotide sequence complementary to an mRNA species that encodes a protein essential for tapetal function, and a 3'-NCCA nucleotide sequence, wherein N is preferably a purine. Id. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region. Id.

Alternatively, antisense genes, ribozyme genes and external guide sequence genes can be regulated by a combination of a tapetum-specific regulatory element and a promoter of an anther-specific gene, which is expressed during the meiotic to quartet stages of development. Preferably, the promoter is the 289 base pair G9 promoter.

B. Restoration of Male Fertility in the F1 Hybrid

The above-described methods can be used to produce transgenic male-sterile maize plants for the production of F1 hybrids in large-scale directed crosses between inbred lines. If all egg cells of the transgenic male-sterile plants do not contain the foreign gene that disrupts tapetal function, then a proportion of hybrids will have a male-fertile phenotype. On the other hand, F1 hybrids will have a male-sterile phenotype if the foreign gene is present in all egg cells of the transgenic male-sterile plants because sterility induced by the foreign gene would be dominant. Thus, it is desirable to use a male fertility restoration system to provide for the production of male-fertile F1 hybrids. Such a fertility restoration system has particular value when the harvested product is seed.

One approach to male fertility restoration would be to cross transgenic male-sterile plants with transgenic male-fertile plants which contain a fertility restoration gene under the control of a tapetum-specific regulatory element. For example, Mariani et al., *Nature* 357:384–387 (1992), crossed male-fertile plants that expressed a barnase inhibitor, designated "barstar," with male-sterile plants that expressed barnase. Hartley, *J. Mol. Biol.* 202:913 (1988), discloses the nucleotide sequence of barstar.

Alternatively, male fertility restoration can be achieved by expressing diptheria toxin ribozymes in male-fertile plants to neutralize the effects of diptheria toxin in male-sterile plants. Thus, male fertility can be restored in the F1 hybrids by producing a male-fertile transgenic plant that synthesizes a particular species of RNA molecule or polypeptide to counteract the effects of the particular foreign gene expressed in the male-sterile transgenic plants.

In an alternative method for restoring male fertility, transgenic male-sterile plants contain an expression vector that comprises the following elements: a tapetum-specific regulatory element, a prokaryotic regulatory element, and a foreign gene capable of disrupting tapetal function. Transgenic male-fertile plants are produced that express a prokaryotic peptide under the control of a tapetum-specific regulatory element. In the F1 hybrids, the prokaryotic peptide binds to the prokaryotic regulatory sequence and represses the expression of the foreign gene which is capable of disrupting tapetal function. An advantage of this approach to fertility restoration is that one form of transgenic male-fertile plant can be used to provide F1 fertility regardless of the identity of the foreign gene that was used to disrupt tapetal function in the transgenic male-sterile plant.

For example, the LexA gene/LexA operator system can be used to regulate gene expression pursuant to the present invention. See U.S. Pat. No. 4,833,080 ("the '080 patent) and Wang et al., *Mol. Cell. Biol.* 13:1805 (1993). More specifically, the expression vector of the male-sterile plant would contain the LexA operator sequence, while the expression vector of the male-fertile plant would contain the coding sequences of the LexA repressor. In the F1 hybrid, the LexA repressor would bind to the LexA operator sequence and inhibit transcription of the foreign gene that encodes a product capable of disrupting tapetal function.

LexA operator DNA molecules can be obtained, for example, by synthesizing DNA fragments that contain the well-known LexA operator sequence. See, for example, the '080 patent, supra, and Garriga et al., *Mol. Gen. Genet.* 236:125 (1992). The LexA gene may be obtained by synthesizing a DNA molecule encoding the LexA repressor. Gene synthesis techniques are discussed above and LexA gene sequences are described, for example, by Garriga et al., supra. Alternatively, DNA molecules encoding the LexA repressor may be obtained from plasmid pRB500, American Type Culture Collection accession No. 67758. Those of skill in the art can readily devise other male fertility restoration strategies using prokaryotic regulatory systems, such as the lac repressor/lac operon system or the trp repressor/trp operon system.

The present invention, thus generally described, will be understood more readily by reference to the following examples, which are provided by way of illustration and are not intended to be limiting of the present invention.

EXAMPLE 1

Identification of a Tapetum-Specific Regulatory Element by Deletion Analysis

Dr. Stephen Goff (U.S. Department of Agriculture; Albany, Calif.) provided a genomic clone which contains a gene designated SGB6. The SGB6 genomic clone had been isolated from a maize W22 genomic library in EMBL3 (Clontech Laboratories, Inc.; Palo Alto, Calif.), using radio-labeled SGB6 cDNA as a probe. Since the SGB6 gene is expressed in the tapetal layer of the maize anther, experiments were performed to determine whether a tapetum-specific regulatory element resides upstream of the SGB6 gene.

To determine the nucleotide sequence of the SGB6 upstream region, a 1339 base pair ApaLI/SmaI DNA fragment containing the upstream region was inserted into the vector, pBluescript® KS+ (Stratagene Cloning Systems; La Jolla, Calif.). See subclone "DP1425" in FIG. 1. Nested deletions of the ApaLI/SmaI fragment were generated using well-known techniques and a kit obtained from Stratagene Cloning Systems, Inc. Briefly, plasmid DNA was digested with either BamHI or EcoRI to produce a 5' single-stranded DNA segment as a starting point for exonuclease III digestion. Plasmid DNA also was digested with either SacI or KpnI to generate a 3' single-stranded DNA segment to protect vector DNA from exonuclease III digestion. Following digestion with exonuclease III, DNA was digested with mung bean nuclease to produce blunt ends. Subclones containing the nested deletions were sequenced by the dideoxy chain-termination method of Sanger et al., *Proc. Natl. Acad. Sci. USA* 74:5463 (1977), using an ABI Sequencer (Applied Biosystems, Inc.; Foster City, Calif.).

Figure 2:
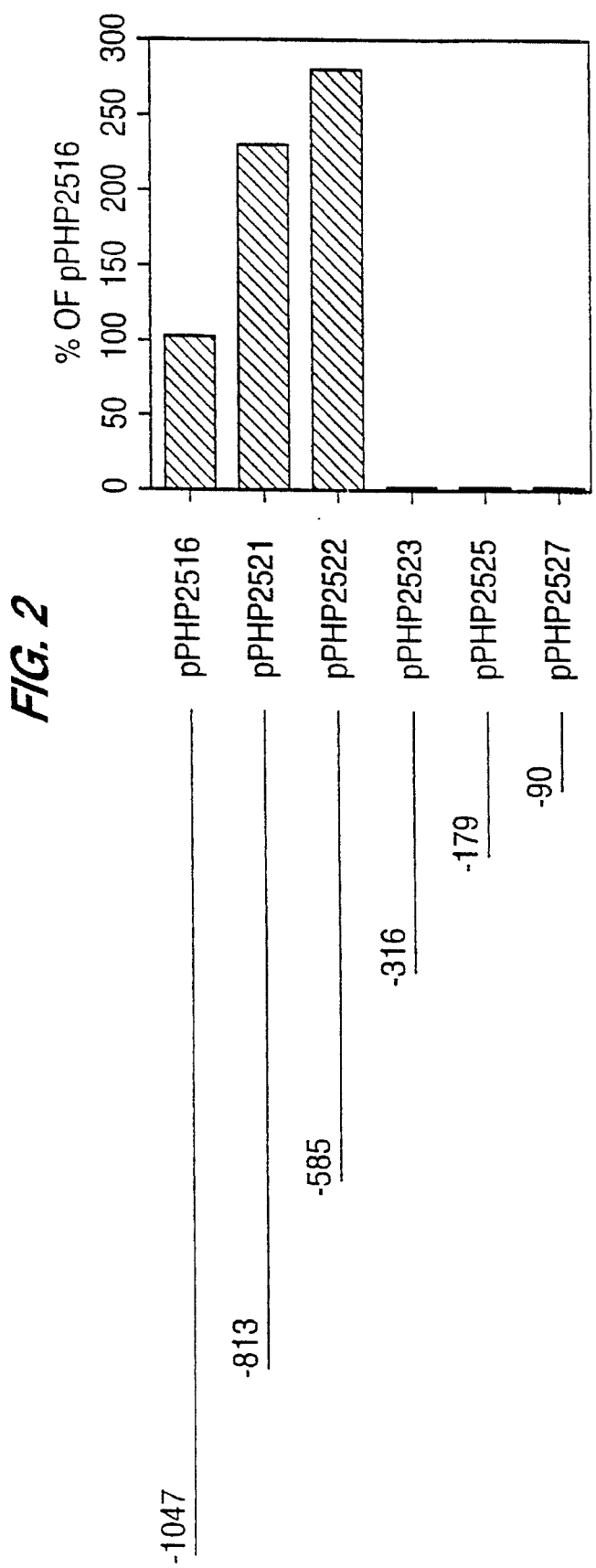
FIG. 2 presents studies on the induction of transient luciferase activity in anther tissue by an SGB6 deletion series.

The function of the putative tapetum-specific regulatory element of the SGB6 gene was characterized by deletion analysis. Deletion plasmids were constructed according to well-known techniques, using exonuclease III and mung bean nuclease digestion. See, for example, Ausubel et al., supra. FIG. 2 shows deletion plasmids obtained by this approach.

Figure 3:
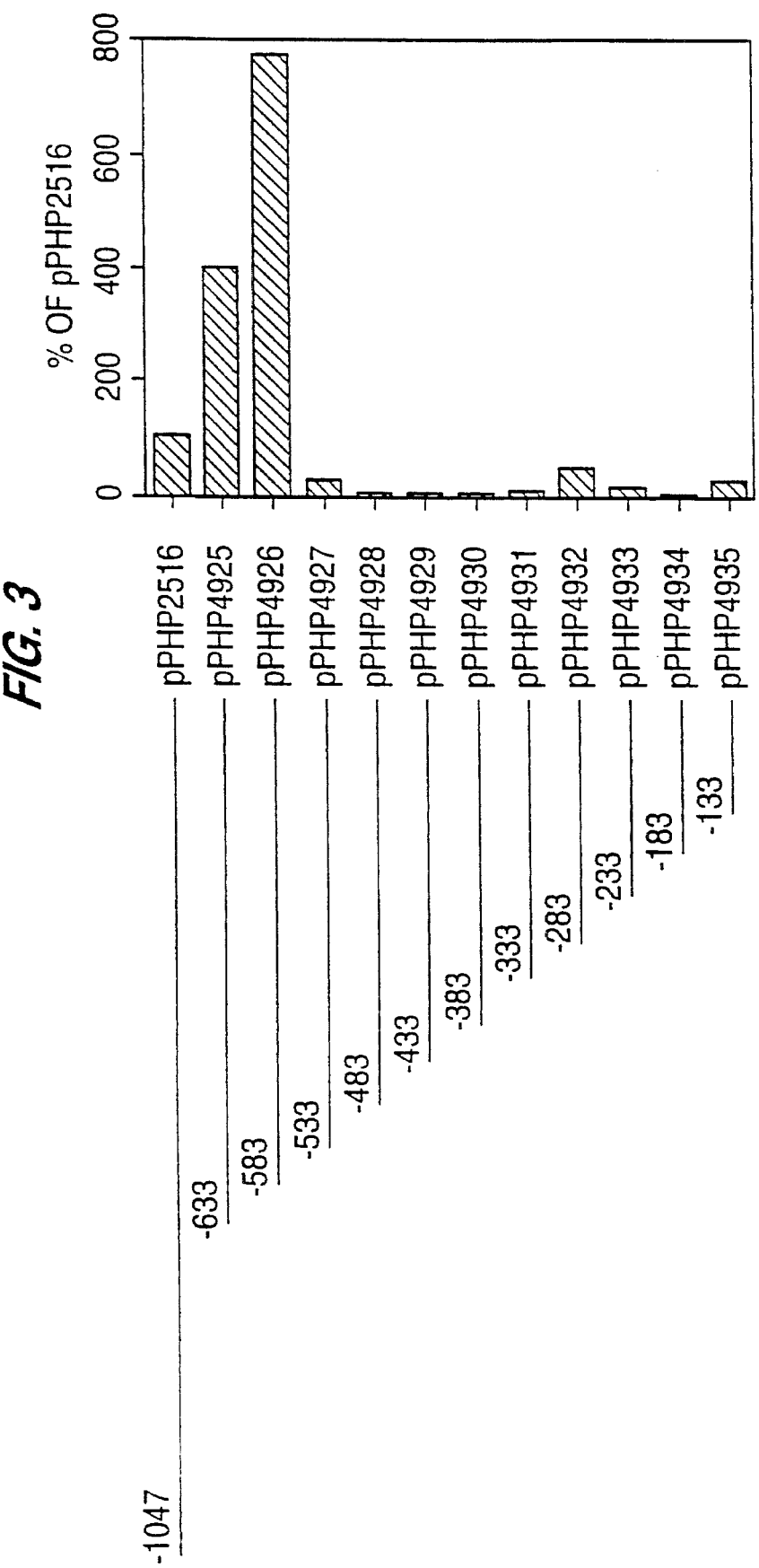
FIG. 3 presents studies on the induction of transient luciferase activity in anther tissue by an SGB6 deletion series.
Figure 4:
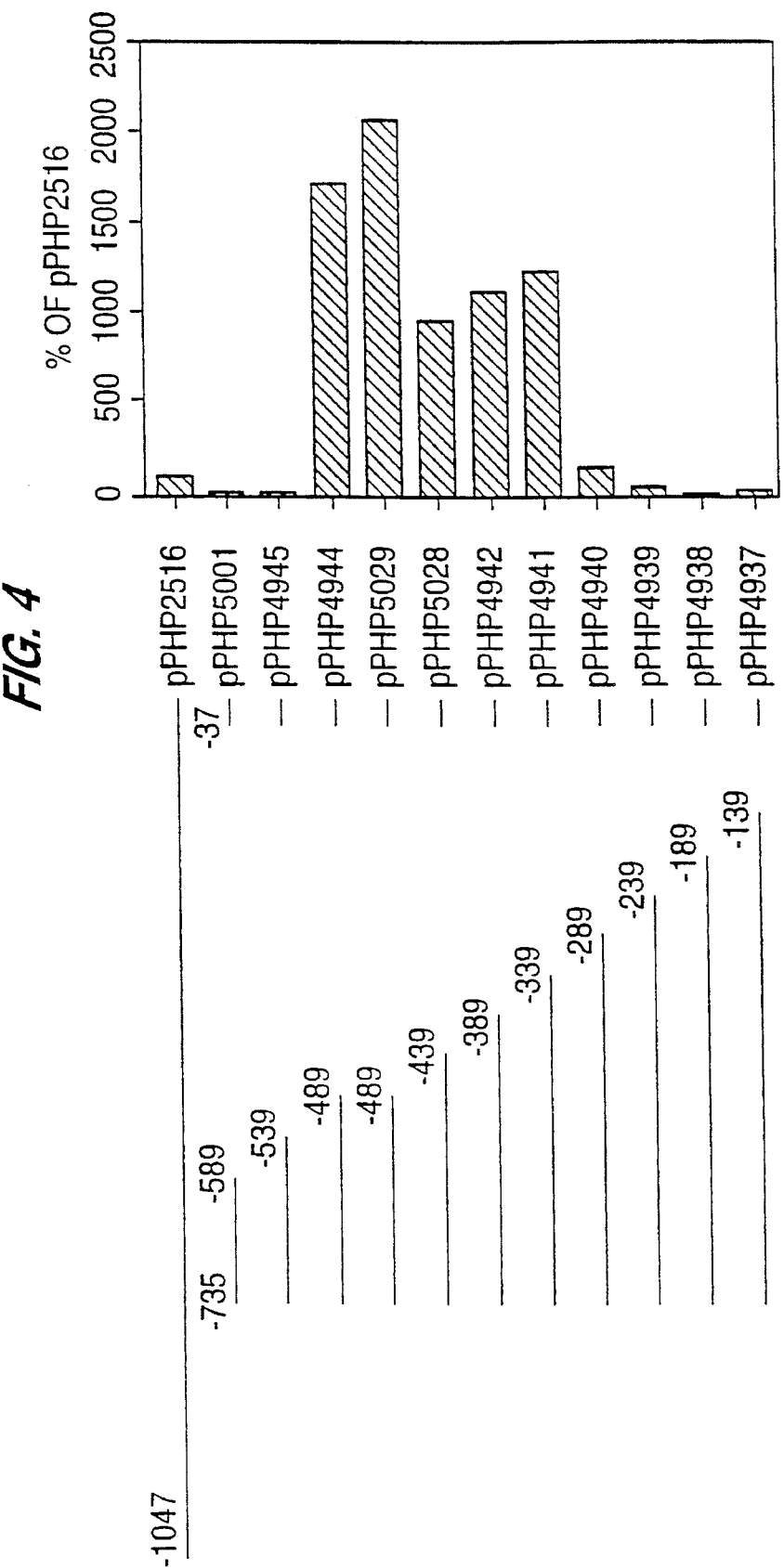
FIG. 4 presents studies on the induction of transient luciferase activity in anther tissue by an SGB6 deletion series in which upstream SGB6 fragments were fused to the SGB6 core promoter.

Deletion plasmids also were obtained by cloning fragments of the putative regulatory region that had been synthesized using the polymerase chain reaction (PCR). FIG. 3 shows a 5' deletion series with endpoints at 50 base pair increments from nucleotides −633 to −33. FIG. 4 shows a 3' deletion series with endpoints at 50 base pair increments from nucleotides −589 to −139.

The function of the deletion plasmids was tested with a transient expression assay using luciferase (LU) as the reporter gene. For these studies, maize anthers were isolated from tassels of *Z. mays* W22 r-g Stadler at various stages of development. One anther from each floret was fixed in Farmer's Solution (3:1; V/V; ethanol/glacial acetic acid) for stage determination. Berlyn et al. BOTANICAL MICROTECHNIQUE AND CYTOCHEMISTRY, page 32 (The Iowa State University Press 1976). Two anthers from each floret were plated on tassel maturation medium, as described by Pareddy et al., *Crop Sci. J.* 29:1564 (1989), which had been solidified with 0.5% GelRite agar (Scott Laboratories, Inc.).

Plasmid DNA was introduced into anther tissue by bombarding the tissue with 1.8μ tungsten particles coated with DNA. Briefly, 10 μg of DNA in a volume of 10 μl were precipitated onto approximately 750 μg (50 μl) of nitric acid-washed tungsten particles by the addition of 50 μl of 2.5M calcium chloride and 20 μl of 0.1M spermidine. The mixture was sonicated and the particles were pelleted by centrifugation, washed in ethanol, and resuspended in 60 μl of ethanol by sonication. Ten microliter aliquots were allowed to dry on macrocarrier disks for bombardment with the PDS-1000 helium particle gun (Bio-Rad Laboratories; Hercules, Calif.), using 1000 PSI rupture disks. Following particle bombardment, anther tissue was incubated at 27° C. in the dark for 16 to 24 hours.

Protein extracts of anther tissue were tested for the presence of luciferase activity using standard techniques. See, for example, De Wet et al., *Mol. Cell. Biol.* 7:725 (1987). Briefly, soluble protein was extracted from anther tissue by grinding the tissue on ice in 100 μl of grinding buffer (50 mM $KPO_4$, 10 mM EDTA, and 2 mM dithiothreitol; pH 7.8). Insoluble debris was removed by centrifuging the mixture for 5 minutes at full speed in a refrigerated microfuge. Typically, a 20 μl aliquot of plant extract was incubated with 200 μl of assay buffer (25 mM Tricine, 15 mM $MgCl_2$, 5 mM ATP, and 500 μg/ml bovine serum albumin) and 100 μl of 500 μM luciferin (potassium salt). Light output was measured in a Monolight 2010 analytical luminometer.

The results of these studies demonstrated that a DNA fragment containing the SGB6 upstream region can induce transient luciferase expression in anthers at the quartet stage and through to the mid-uninucleate stage of anther development. In contrast, little or no luciferase activity was detected in premeiotic anthers. Furthermore, the results demonstrated that a DNA fragment containing nucleotides −735 to −489 upstream of the SGB6 transcriptional start site in combination with the SGB6 core promoter (i.e., the first 37 nucleotides upstream of the transcriptional start site) can induce a high level of luciferase expression in anther tissue. See FIG. 4. Finally, the results shown in FIG. 3 indicate that a regulatory element is located within nucleotides −583 to −483.

EXAMPLE 2

Characterization of the 94 Base Pair Tapetum-Specific Regulatory Element

Figure 5:
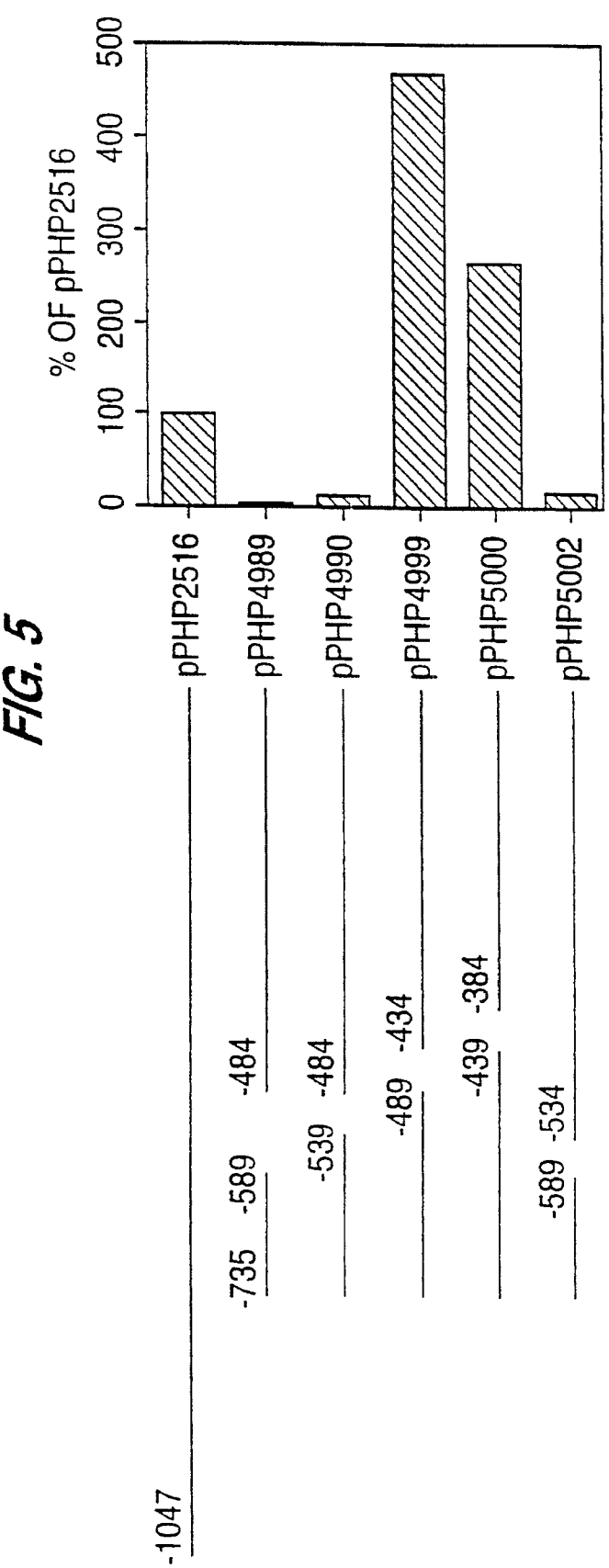
FIG. 5 presents studies on the induction of transient luciferase activity in anther tissue by upstream SGB6 DNA fragments containing internal deletions.

Upon identification of an approximately 100 base pair upstream region involved in high-level gene expression in anther tissue, DNA fragments containing internal deletions were generated using the 5' and 3' deletion plasmids, described above. FIG. 5 shows that DNA fragments containing internal deletions either lacked the entire 100 base pair region or lacked portions of the 100 base pair region. A comparison of the results obtained with plasmids DP4989 and DP4999 indicated that a regulatory element resides in the region extending from about nucleotide −588 to nucleotide −489.

The SGB6 regulatory region was further characterized by synthesizing a 94 base pair DNA fragment containing nucleotides −583 to −490, fusing the 94 base pair fragment upstream of the SGB6 core promoter, and inserting the resultant DNA fragment into a luciferase vector. See FIG. 6. Additional vectors were constructed with multiple copies of the 94 base pair region, with the 94 base pair region positioned in reverse orientation with respect to the promoter, and with portions of the 94 base pair region spanning 32 or 45 base pairs of the middle of the 94 base pair region. A control plasmid contained the CaMV 35S promoter, Tobacco Mosaic Virus nontranslated leader region Ω', and the first intron of the maize ADH1 gene, which was fused to the luciferase gene. All constructs contained a 3' transcript processing region from the Proteinase Inhibitor II (PinII) gene of potato.

Figure 6:
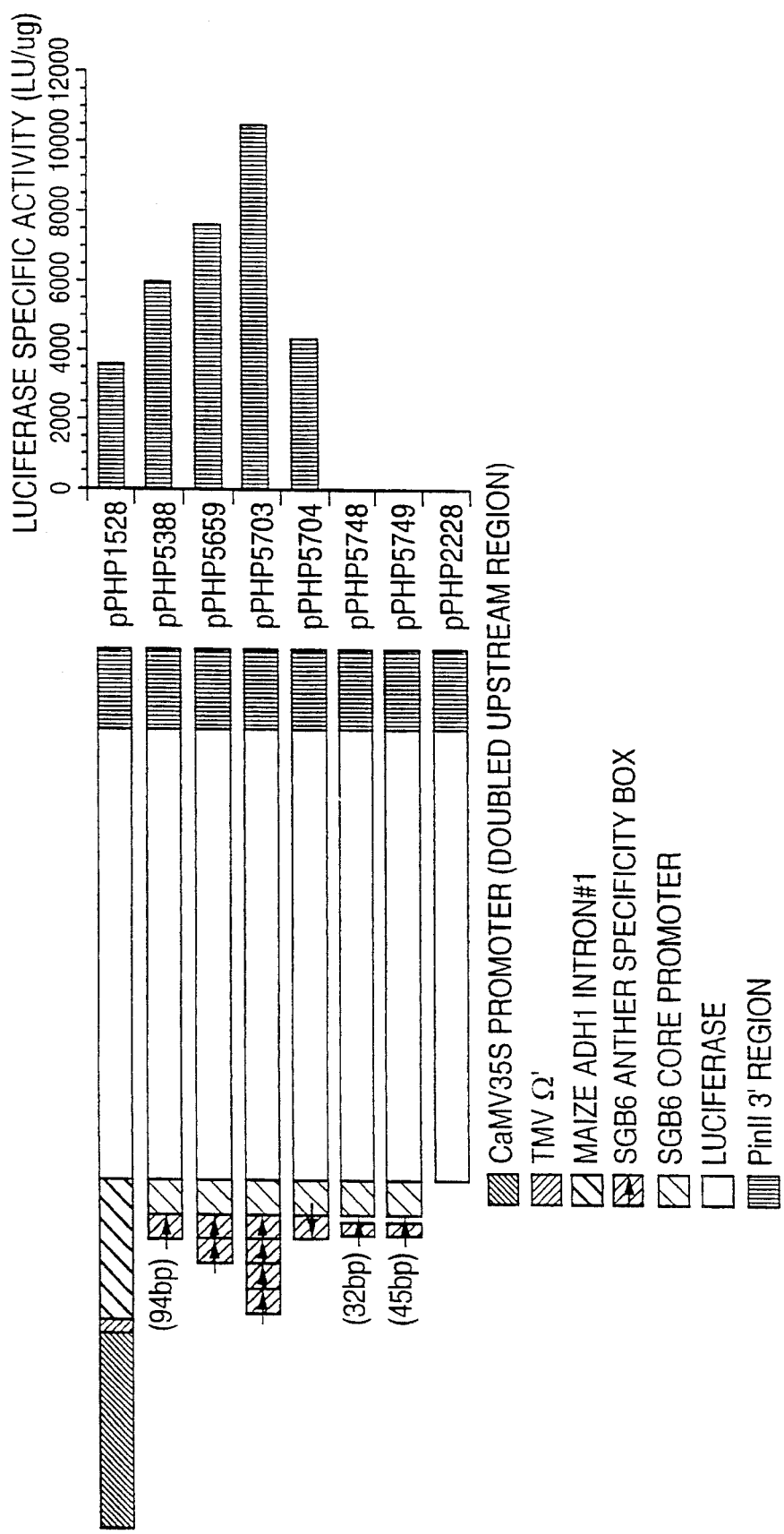
FIG. 6 presents studies on the induction of luciferase (LU) activity by a control plasmid or by test plasmids containing the 94 base pair tapetum-specific regulatory element ("SGB6 Anther Specificity Box"), or portions thereof. The control plasmid contained a CaMV 35S promoter, a Tobacco Mosaic Virus (TMV) nontranslated leader region $\Omega'$, the first intron of the maize alcohol dehydrogenase 1 (ADH1) gene, and the luciferase gene. All plasmids contained a 3' transcript processing region from the potato Proteinase Inhibitor II (PinII) gene fused downstream of the luciferase gene.

As shown in FIG. 6, constructs containing the 94 base pair fragment fused to the SGB6 core promoter can induce gene expression. Gene expression was increased by doubling or quadrupling the number of copies of the 94 base pair fragment upstream of the core SGB6 promoter. Moreover, insertion of the 94 base pair fragment in the reverse orientation also induced gene expression. Thus, the results indicate that the 94 base pair fragment induces gene expression in a position and orientation independent manner, which are characteristics of an enhancer.

Experiments were performed to determine whether a plasmid containing the 94 base pair regulatory element can induce transient luciferase activity in coleoptiles, roots, or embryogenic tissue. Coleoptiles and roots were obtained by sterilizing the surfaces of B73 seedlings with 20% bleach, rinsing the seedlings twice with sterile distilled water, and allowing the seedlings to absorb water for one to three hours. The seedlings germinated in the dark at 28° C. for 48 hours. The germinated embryo and scutellum were excised from the seeds and plated on Murashige and Skoog medium containing 0.5 mg/l zeatin and 0.3% GelRite agar. Tissues were bombarded with DNA-coated tungsten particles as described above and embryos were incubated for 18–20 hours at 28° C. in the dark. Coleoptiles and roots were excised from the germinated seedlings immediately prior to homogenizing the tissue for the luciferase assay, which was performed as described above.

Embryogenic suspensions were maintained at 28° C. in the dark by subculturing the tissue twice weekly in medium containing MS salts and 2.0 mg/l of 2,4-dichlorophenoxy acetic acid. Murashige et al., *Physiol. Plant* 15:473 (1962). Before particle bombardment, cultures were homogenized and resuspended in Murashige and Skoog medium containing 0.5 mg/l zeatin, 0.3% GelRite agar, and 0.25M mannitol. Cultures were incubated in the dark at 28° C. either for 5 hours or overnight with shaking before particle bombardment. After bombardment, cultures were transferred to medium containing AT base medium, proline (700 mg/l), 2,4-dichlorophenoxy acetic acid (0.75 mg/l), and 0.3% GelRite agar. AT base medium is composed of the following components (grams/100 liter water): potassium nitrate (160), anhydrous magnesium sulfate (12.2), ammonium sulfate (170), $FeSO_4 \cdot XH_2O$ (2.039), disodium EDTA (2.78), potassium iodide (0.075), boric acid (0.3), $MnSO_4 \cdot H_2O$ (1.0), $ZnSO_4 \cdot H_2O$ (0.125), $Na_2 \cdot MoO_4 \cdot 2H_2O$ (0.025), anhydrous cupric sulfate (0.0016), anhydrous cobalt chloride (0.0014), anhydrous calcium chloride (22.65), potassium phosphate monobasic (30.0), pyridoxine HCl (0.05), thiamine HCl (0.1). nicotinic acid (niacin; 0.05), and glycine (0.2). Cultures were incubated for 18–24 hours at 28° C. in the dark.

A control plasmid containing a CaMV 35S promoter upstream of the luciferase gene induced strong luciferase activity in anther tissue, coleoptiles, roots, and embryogenic suspensions. See FIG. 7. In contrast, test plasmids containing the 94 base pair fused to either the SGB6 core promoter or the CaMV 35S core promoter induced strong luciferase activity in anthers, but little or no luciferase activity in coleoptiles, roots, or embryogenic suspensions. Thus, the 94 base pair regulatory element can regulate the function of the SGB6 promoter or a heterologous promoter in an anther specific-manner.

EXAMPLE 3

In Vivo Expression of a Reporter Gene Controlled by a Tapetum-Specific Regulatory Element The function of the SGB6 regulatory region was examined by producing transgenic maize plants containing a GUS expression vector under the control of tapetum-specific regulatory sequences. The vectors also contained a 3' nos transcriptional processing region downstream of the GUS reporter gene. Transgenic plants were Obtained by particle bombardment of either a GS2 maize embryogenic suspension culture (Pioneer Hi-Bred International, Inc.; Des Moines, Iowa) or callus tissue obtained from Hi-II, a proprietary variety of maize (Pioneer Hi-Bred International, Inc.). The GS2 culture was maintained in a medium containing MS salts and 2 mg/ml of 2,4-dichlorophenoxy acetic acid. The callus tissue was maintained on solid medium containing N6 salts [Chu et al., *Sci. Sin.* 18:659 (1975)], 1 mg/ml of 2,4-dichlorophenoxy acetic acid, 25 mM proline, and 0.2% GelRite agar.

Before particle bombardment, embryogenic tissue was suspended for four hours in the above-described medium with 0.25M mannitol and then transferred to sterile 3 MM filter paper disks, wetted with 0.5 ml of the medium. Typically, tissues were bombarded at 650 PSI with acid-washed 1.8µtungsten particles precipitated with 0.1 to 10 µg of DNA, as described above. In these experiments, tungsten particles were coated with a 1:1 mixture of a test plasmid and a selection plasmid. The test plasmid contained an SGB6-GUS construct, while the selection plasmid contained the phosphinothricin-N-acetyl transferase gene fused to a CaMV35S promoter. Selection was performed using the above-described medium, solidified with 0.2% GelRite agar and containing 3 mg/ml Bialaphos (phosphinothricin).

GUS activity was measured using a standard technique. Jefferson, *Plant Mol. Biol. Rep.* 5:387 (1987).

The test plasmid introduced into GG2, pPHP2125, contained the SGB6 5' region from nucleotide −1047 to nucleotide +100, which was fused to the GUS reporter gene. The results of these experiments demonstrated that the SGB6 regulatory region can induce GUS gene expression in the tapetal layer of the anther of a transgenic plant. In contrast, the SGB6 regulatory region did not induce GUS gene expression in leaves or roots of transgenic plants. GUS gene expression was not observed in anthers of control plants transformed with the phosphinothricine resistance gene expression vector, alone.

The test plasmid introduced into Hi-II tissue, pPHP5390, contained the SGB6 5' region from nucleotide −735 to nucleotide −489, the SGB6 core promoter region from nucleotide −37 to nucleotide +100, and the GUS reporter gene. The results indicated that the SGB6 regulatory region can induce GUS gene expression in Hi-II anthers of transgenic plants. GUS gene expression was not observed in anthers of control plants transformed with the phosphinothricine resistance gene selection vector, alone.

EXAMPLE 4

The Use of a G9 Promoter to Extend the Developmental Window of Tapetum-Specific Gene Expression To extend the developmental window of tapetum-specific gene expression, promoter sequences were obtained from an anther-specific gene, designated "G9" which is expressed during the meiotic to quartet stages of development. G9 promoter sequences were isolated using general methods described above. Briefly, G9 cDNA was obtained by the subtractive hybridization technique using a maize ear shoot cDNA library and a maize tassel cDNA library in which the most mature anthers were in meiosis. The G9 cDNA was used as a probe to isolate the G9 genomic clone. The orientation of genomic sequences corresponding to the G9 cDNA clone was determined and the upstream region of the G9 gene was sequenced.

Studies with G9 upstream sequences fused to a luciferase reporter gene indicated that the G9 promoter induces gene expression in anthers during meiosis and through to the quartet stage of development. See FIG. 8. Deletion analyses identified a 289 base pair fragment that extends from the start of translation to 192 nucleotides upstream of the putative TATA box and that contains the G9 promoter. The nucleotide sequence of the 289 base pair G9 promoter is presented in FIG. 9 [SEQ ID NO: 2].

An expression vector was constructed comprising the following elements in sequence: the 94 base pair tapetum-specific regulatory element ("SGB6 Anther Specifity Box"), the 289 base pair G9 promoter, and the luciferase gene. The expression vector was introduced into anther tissue and transient luciferase gene expression was assayed as described above.

As shown in FIG. 8, the combination of the tapetum-specific regulatory element and the G9 promoter extended the developmental window for luciferase gene expression. The chimeric regulatory construct provided tapetum-specific gene expression during meiosis and through to the mid-uninucleate stage of development.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

promoter and the CaMV 35S core promoter.

5. The expression vector of claim 5, wherein said promoter is the SGB6 core promoter.

6. The expression vector of claim 3, wherein said promoter is an isolated DNA molecule comprising the nucleotide sequence of SEQ ID NO:2, wherein said DNA molecule is a promoter of an anther-specific gene which is expressed during the meiotic to quartet stages of development.

7. The expression vector of claim 3, further comprising a foreign gene, wherein said foreign gene is operably linked to said promoter.

8. The expression vector of claim 7, wherein the product of said foreign gene disrupts the function of tapetal cells.

What is claimed is:

1. An isolated DNA molecule comprising the nucleotide sequence of SEQ ID NO:1, wherein said DNA molecule is a tapetum-specific regulatory element.

2. An expression vector comprising a tapetum-specific regulatory element of claim 1.

3. The expression vector of claim 2, further comprising a promoter, wherein the function of said promoter is under the control of said tapetum-specific regulatory element.

4. The expression vector of claim 4, wherein said promoter is selected from the group consisting of the SGB6 core promoter and the CaMV 35S core promoter.

9. The method of claim 1, wherein said structural gene encodes a protein selected from the group consisting of diphtheria toxin, *Aspergillus oryzae* RNase-T1, barnase and callase.

10. A method of using the expression vector of claim 9 to produce a male-sterile plant, comprising the steps of (a) introducing said expression vector into embryogenic plant cells, wherein said foreign gene is selected from the group consisting of a structural gene, an antisense gene, a ribozyme gene and an external guide sequence gene, and (b) producing a plant from said embryogenic plant cells, wherein said plant expresses said foreign gene.

11. The method of claim 1, wherein the product of said antisense gene is selected from the group consisting of callase antisense RNA and chalcone synthase A RNA.

12. The method of claim 1, wherein said ribozyme gene comprises callase nucleotide sequences.

13. The method of claim 1, wherein said external guide sequence gene comprises callase nucleotide sequences.

14. The method of claim 1, wherein said embryogenic plant cells are embryogenic maize cells.

15. A method of producing a male-sterile plant, comprising the step of:

(a) constructing an expression vector comprising a tapetum-specific regulatory element, a promoter, and a foreign gene, wherein said tapetum-specific regulatory element comprises the nucleotide sequence of SEQ ID NO:1, wherein said tapetum-specific regulatory element in conjunction with said promoter control the expression of said foreign gene, and wherein the product of said foreign gene disrupts the function of tapetal cells, thereby producing a male-sterile plant.

16. The method of claim 15, further comprising the step of:

(b) introducing said expression vector into embryogenic plant cells.

17. A method of using a tapetum-specific regulatory element to produce a male-fertile hybrid plant, comprising the steps of:

(a) producing a first parent male-sterile plant comprising an expression vector that comprises the tapetum-specific regulatory element of claim 1, a promoter, and a first foreign gene, wherein said tapetum-specific regulatory element in conjunction with said promoter control the expression of said first foreign gene, and wherein the product of said first foreign gene disrupts the function of tapetal cells;

(b) producing a second parent plant comprising an expression vector that comprises said tapetum-specific regulatory element, a promoter and a second foreign gene, wherein said tapetum-specific regulatory element in conjunction with said promoter control the expression of said second foreign gene; and (c) cross-fertilizing said first parent with said second parent to produce a hybrid plant, wherein the tapetal cells of said hybrid plant express said second foreign gene, and wherein the product of said second foreign gene prevents the disruption of tapetal function by the product of said first foreign gene, thereby producing a male-fertile hybrid plant.

18. The method of claim 17, wherein said first foreign gene encodes barnase and said second foreign gene encodes a barnase inhibitor.

19. The method of claim 17, wherein said product of said first foreign gene is diphtheria toxin and said product of said second foreign gene is a diphtheria toxin ribozyme.

20. The method of claim 1, wherein said promoter is an isolated DNA molecule comprising the nucleotide sequence of SEQ ID NO:2.

* * * * *

UNITED STATES PATENT AND TRADEMARK OFFICE
CERTIFICATE OF CORRECTION

PATENT NO. : 5,470,359
DATED : November 28, 1995
INVENTOR(S) : Gary A. HUFFMAN

It is certified that error appears in the above-indentified patent and that said Letters Patent is hereby corrected as shown below:

In claim 4, line 1, the term "claim 4" should be --claim 3--.

In claim 5, line 1, the term "claim 5" should be --claim 4--.

In claim 9, line 1, the term "claim 1" should be --claim 9--.

Claim 9 should be renumbered as claim 10.

In claim 10, line 1, the term "claim 9" should be --claim 8--.

Claim 10 should be renumbered as claim 9.

In claim 11, line 1, the term "claim 1" should be --claim 9--.

In claim 12, line 1, the term "claim 1" should be --claim 9--.

In claim 13, line 1, the term "claim 1" should be --claim 9--.

In claim 14, line 1, the term "claim 1" should be --claim 9--.

UNITED STATES PATENT AND TRADEMARK OFFICE
CERTIFICATE OF CORRECTION

PATENT NO. : 5,470,359

DATED : November 28, 1995

INVENTOR(S) : Gary A. Huffman

It is certified that error appears in the above-indentified patent and that said Letters Patent is hereby corrected as shown below:

In claim 20, line 1, the term "claim 1" should be --claim 9--.

Signed and Sealed this

Eleventh Day of March, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 94 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ACAGTTCACT  AGATATGCAT  GATCTTTAAC  AATTGCTGCT  GGATTGTGCG  GTTTCTTTTG         60

GCACAAATGG  CATGAACAGA  GTAATCCGGG  ACGC                                      94
```

( 2 ) INFORMATION FOR SEQ ID NO:2:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CCTTCGAACG  AACGGTACTG  TAAAAATACG  GTAGCTCAGA  TTTGTGATTT  CAATTCGATT         60

CGGGTCTCCT  GGCTGGATGA  AACCGATGCG  AGAGAAGAAA  AAAAAATTGT  TGCATGTAGT        120

TGGCGCCTGT  CACCCAACCA  AACCAGTAGT  TGAGGCACGC  CCTGTTTGCT  CACGATCACG        180

AACGTACAGC  ACTATAAAAC  ACGCAGGGAC  TGGAAAGCGA  GATTTCACAG  CTGAAACGAG        240

CCAAAACGCA  GAAGCTGCAC  TGCATACATC  GAGCTAACTA  TCTGCAGCCA  TG                292
```